United States Patent [19]
Slater et al.

[11] Patent Number: 5,507,297
[45] Date of Patent: Apr. 16, 1996

[54] ENDOSCOPIC INSTRUMENTS HAVING DETACHABLE PROXIMAL HANDLE AND DISTAL PORTIONS

[75] Inventors: Charles R. Slater, Fort Lauderdale; Jurgen A. Kortenbach, Miami; Herbert Cohen, Fort Lauderdale; George Nunez, Miami, all of Fla.

[73] Assignee: Symbiosis Corporation, Miami, Fla.

[21] Appl. No.: 16,596

[22] Filed: Feb. 11, 1993

Related U.S. Application Data

[63] Continuation-in-part of Ser. No. 680,392, Apr. 4, 1991, Pat. No. 5,192,298, and a continuation-in-part of Ser. No. 989,984, Dec. 4, 1992, Pat. No. 5,293,878, which is a continuation of Ser. No. 833,842, Feb. 7, 1992, abandoned, and a continuation of Ser. No. 998,951, Dec. 31, 1992.

[51] Int. Cl.$^6$ ........................................ A61B 10/00
[52] U.S. Cl. ........................................ 128/751; 606/205
[58] Field of Search ............................... 128/4, 6, 749, 128/751, 754, 755; 606/207, 208, 205, 206; 16/114 R, DIG. 12, DIG. 24; 7/167; 30/260; 74/557, 528, 527, 523, 525, 543, 545

[56] References Cited

U.S. PATENT DOCUMENTS

| | | | |
|---|---|---|---|
| 2,113,246 | 4/1938 | Wappler | 606/205 |
| 2,790,437 | 4/1957 | Moore . | |
| 4,043,323 | 8/1977 | Komiya | 128/4 |
| 4,763,668 | 8/1988 | Macek et al. | 128/751 |
| 4,815,476 | 3/1989 | Clossick | 128/751 |
| 5,100,430 | 3/1992 | Avellanet et al. | 128/751 X |
| 5,160,343 | 11/1992 | Brancel et al. | 128/751 X |
| 5,201,752 | 4/1993 | Brown et al. | 606/207 X |
| 5,282,800 | 2/1994 | Foshee et al. | 606/52 |
| 5,282,806 | 2/1994 | Haber et al. | 606/139 |

FOREIGN PATENT DOCUMENTS

| | | | |
|---|---|---|---|
| 66465 | 12/1982 | European Pat. Off. . | |
| 512725 | 11/1992 | European Pat. Off. | 606/205 |

*Primary Examiner*—Lee S. Cohen
*Assistant Examiner*—Samuel Gilbert
*Attorney, Agent, or Firm*—David P. Gordon

[57] ABSTRACT

An endoscopic instrument has a distal assembly removable from a proximal handle. The distal assembly includes a tube carrying an end effector and a push rod coupled to the end effector and slidable through the tube. The proximal handle includes a tube sleeve for receiving the tube, an actuator and a latch for coupling the push rod to the actuator. The tube sleeve is provided with a tube lock for holding the tube securely in place and the tube is provided with a circumferential groove for engaging the lock. The latch is spring loaded, hinged, and has an inclined surface for quick coupling with the push rod. The latch also has a mechanism for uncoupling the latch from the push rod. The push rod is provided with a mating tip which engages the latch so that the actuator causes reciprocal movement of the push rod within the tube to operate the end effector. An axially movable collar on the tube sleeve is used in unlatching, and in one arrangement is also used for rotating the distal assembly.

53 Claims, 8 Drawing Sheets

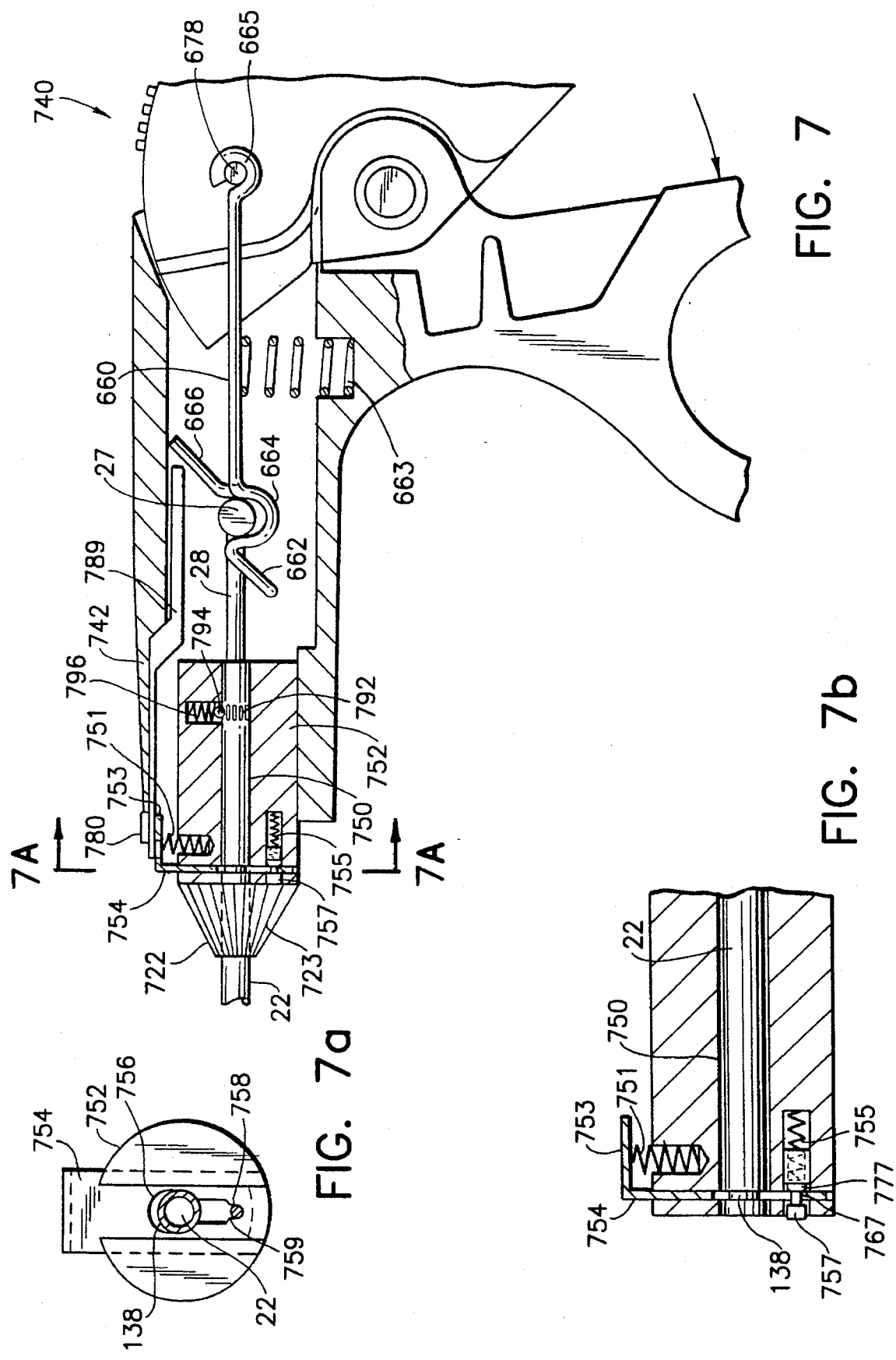

ENDOSCOPIC INSTRUMENTS HAVING DETACHABLE PROXIMAL HANDLE AND DISTAL PORTIONS

This application is a continuation-in-part of co-assigned U.S. Ser. Nos. 07/680,392 filed Apr. 4, 1991, now U.S. Pat. No. 5,192,298, 07/989,984 filed Dec. 4, 1992, now U.S. Pat. No. 5,293,878 (which is a continuation of U.S. Ser. Nos. 07/833,842 filed Feb. 7, 1992 now abandoned), and 07/998,951 filed Dec. 31, 1992 and is related to U.S. Pat. No. 5,174,300, the complete disclosures of which are incorporated herein by reference.

BACKGROUND OF THE INVENTION

This invention relates to surgical instruments. More particularly, this invention relates to endoscopic surgical instruments having detachable proximal and distal portions.

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera or magnifying lens is often inserted through the largest diameter trocar tube (e.g. 10 mm diameter), while a cutter, dissector, or other surgical instrument is inserted through a smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the camera in place in the larger trocar tube.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. (As used herein, "proximal" means closest to the surgeon and farthest from the surgical site, while "distal" means farthest from the surgeon and closest to the surgical site.) The end effectors take many forms such as grippers, cutters, forceps, dissectors and the like. Some endoscopic instruments are provided with a ferrule on the tube so that the tube which carries the end effectors can be rotated relative to the handle. Initially, endoscopic surgical instruments were very expensive, at least partly because they had to be made very small but still be durable and reliable.

Recently, a number of "disposable" endoscopic instruments have been introduced and their use is now widely accepted. One of the advantages of disposable endoscopic instruments over reusable instruments is that because they are used only a single time, there are no sterilization problems, and no concerns about the dulling or nicking of blades or wearing of parts. However, in order to justify disposing of instruments after a single use, the instruments have to be much less expensive than the reusable tools. In order to manufacture the instruments less expensively, the disposable instruments typically use less expensive materials. As a result, the disposable instruments are less durable than the reusable instruments. Typically, the less durable components of the disposable instruments are most often the distal end effectors. However, the distal end effectors are not so fragile that they can only withstand a single use. Some surgeons therefore sterilize disposable instruments and reuse them a few times in order to reduce "per procedure costs". In addition, it will be appreciated by those skilled in the art that the proximal handle portion of the disposable instrument, is often nearly as durable as the proximal handle portion of a reusable instrument. Ultimately, therefore, it is the distal portion of the instrument which wears or breaks and mandates disposal of the entire instrument.

SUMMARY OF THE INVENTION

It is therefore an object of the invention to provide an endoscopic instrument having detachable distal and proximal portions which permits separate disposal or reuse of the distal and proximal portions.

It is also an object of the invention to provide different mechanisms for easily connecting and disconnecting a distal portion and a proximal handle portion of an endoscopic instrument.

It is another object of the invention to provide an endoscopic instrument having a proximal handle, and a distal portion having an outer tube, a push rod, and distal end effectors coupled to the push rod and tube, wherein the distal portion is removably coupled to the proximal handle.

It is a further object of the invention to provide an endoscopic instrument with a proximal handle portion, and a distal end portion which is separable from the proximal handle portion, where the distal end portion can be rotated relative to the proximal handle portion.

In accord with these objects which will be discussed in detail below, the endoscopic instrument of the present invention broadly includes a distal assembly which engages and is detachable from a proximal handle assembly. The distal assembly includes an outer tube, a push rod which extends through the tube, and end effectors which are coupled to both the push rod and the tube. The proximal handle assembly includes a tube sleeve for receiving the tube, manually operable actuating means, and a latch for coupling the push rod to the actuating means. The tube sleeve is preferably provided with a ball bearing or blade lock for holding the tube securely in place, and the tube is preferably provided with a circumferential groove for engaging the ball bearing or blade lock. The latch of the proximal handle assembly is preferably spring loaded and hinged, and is provided with an inclined surface for "quick-coupling" with the push rod. Unlatching is accomplished either via an unlatching surface which when biased by an unlatching member uncouples the push rod, or a cam surface which permits rotation of the latch member into an unlatching position. The push rod is provided with a mating tip which engages the latch so that the manually operable actuating means causes reciprocal movement of the push rod within the tube to operate the end effectors when the push rod and latch are engaged.

Preferred aspects of the reusable-disposable endoscopic instrument include: providing a biased collar around the tube sleeve of the proximal handle, where the biased collar includes ferrule engaging means which in its biased position engages a ferrule on the tube and thereby permits rotation of the tube; providing the interior of the biased collar with a stepped diameter to receive the balls of the ball lock when the biased collar is retracted to uncouple the tube; providing a cammed surface which engages the latch so that the latch rotates into a disengaging (unlatching) position when the push rod is forced in a distal direction; forming the latch as a U-shaped hook and the mating tip of the push rod as a grooved cone or a ball; and providing a spring biased bushing within the sleeve for engaging the ball lock when the tube is removed from the sleeve; and providing the tube with a proximal ferrule for embracing the collar on the handle when the tube is coupled to the handle.

Additional objects and advantages of the invention will become apparent to those skilled in the art upon reference to the detailed description taken in conjunction with the provided figures.

BRIEF DESCRIPTION OF THE DRAWINGS

FIG. 3b is front view of the latch of FIG. 3a looking in the direction B in FIG. 3a;

FIG. 7 is a view similar to FIG. 6 of another embodiment of the invention utilizing a different tube locking mechanism;

FIG. 7a is a cross sectional view along line 7—7 of FIG. 7;

FIG. 7b is an enlarged view of the blade lock portion of FIG. 7;

DETAILED DESCRIPTION OF THE PREFERRED EMBODIMENTS

Figure 1:
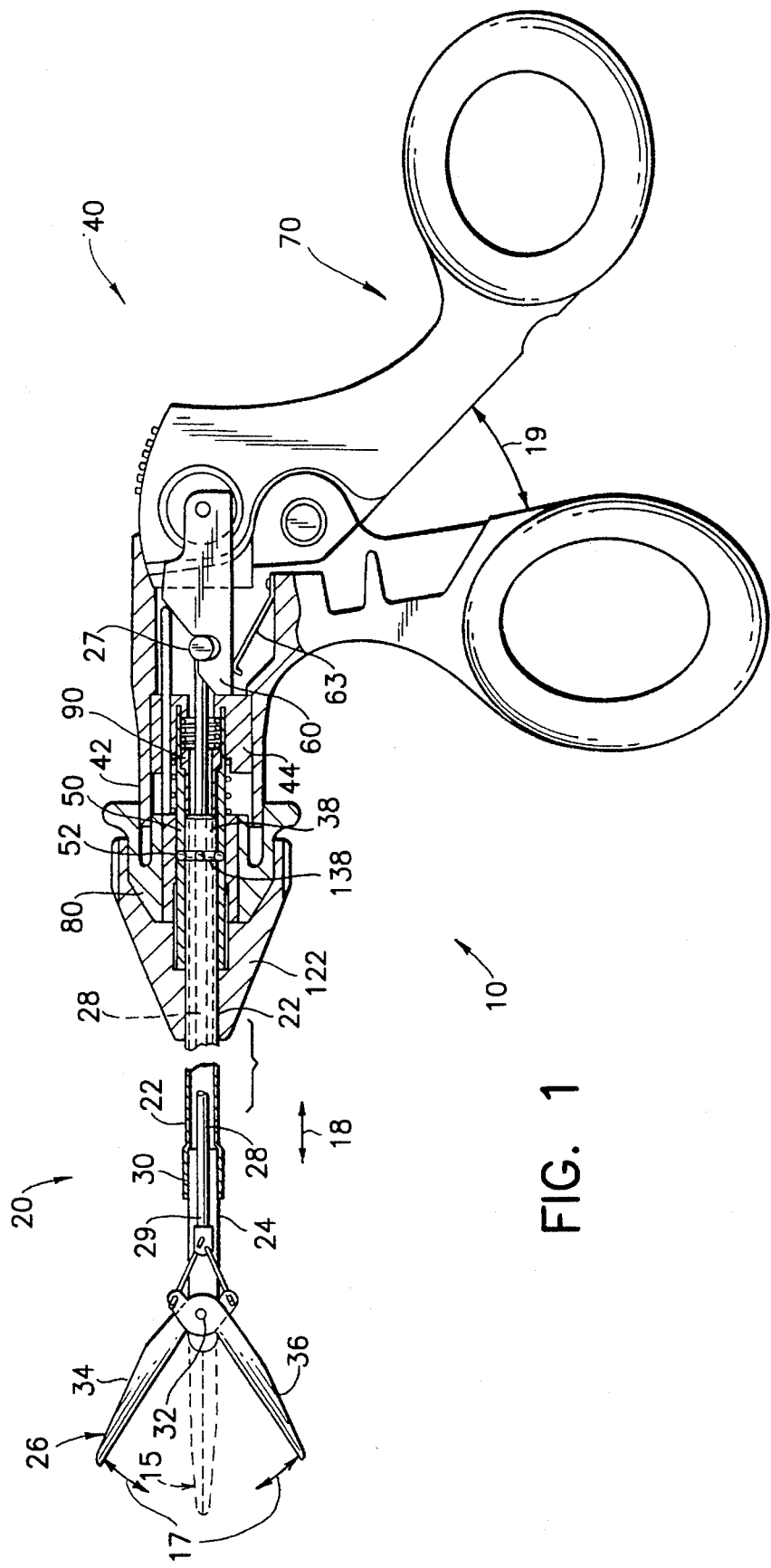
FIG. 1 is an partial side elevation and partial cross sectional view of an endoscopic instrument having detachable handle and distal portions according to the invention.

Referring now to FIG. 1, an endoscopic instrument 10 is seen and generally includes a distal portion 20 and a proximal handle portion 40, with the distal portion 20 being detachable from the handle portion 40. FIG. 1 shows these two portions coupled, although the distal portion 20 is shown with a broken line as it is often much longer than pictured in FIG. 1.

The distal portion 20 of the endoscopic instrument 10 generally includes an aluminum tube 22, a clevis 24, an end effector mechanism 26, and a push rod 28. The clevis 24 is preferably a separately formed aluminum piece which fixedly engages the distal end 30 of aluminum tube 22 and also engages the end effectors 26. The end effectors 26 generally include two members 34, 36 at least one of which is pivotally engaged to clevis 24 at a pivot pin 32. The pivoting member 34 is typically coupled to the distal end 29 of the push rod 28.

The proximal handle portion 40 (described in more detail below with reference to FIG. 2) of the endoscopic instrument 10 generally includes a mouth 42, a sleeve block 44, a tube receiving sleeve 50, tube locking means 52, actuating means 70, and push rod latch 60. The tube sleeve 50 and sleeve block 44 are housed in the mouth 42, and the tube sleeve 50 carries the tube locking means 52. The push rod latch 60 is coupled to the actuating means 70.

In accord with a preferred aspect of the invention, the proximal end 38 of tube 22 disengagably engages sleeve 50 and tube locking means 52 of the handle portion 40 (as will be described in detail hereinafter). In the embodiment of FIG. 1, the proximal end 38 of tube 22 is provided with a ferrule 122 for easy handling during coupling and uncoupling. Because the ferrule is coupled to the tube 22, the ferrule is used for rotation of the tube 22 and end effector 26 relative to the handle 40. The proximal end of the push rod 28, on the other hand, is provided with a proximal end mating tip 27 which removably couples to the latch 60 of the actuating means 70 in the handle portion 40.

In use, the endoscopic instrument of FIG. 1 is typically inserted with the members 34, 36 of the end effector 26 in the closed position 15, through a trocar tube (not shown) into a body cavity (not shown). The members 34, 36 can be opened and closed, as indicated by arrows 17, by reciprocal motion of push rod 28, as indicated by arrows 18, which results from operation of the manual actuating means 70 as indicated by arrows 19.

Figure 2:
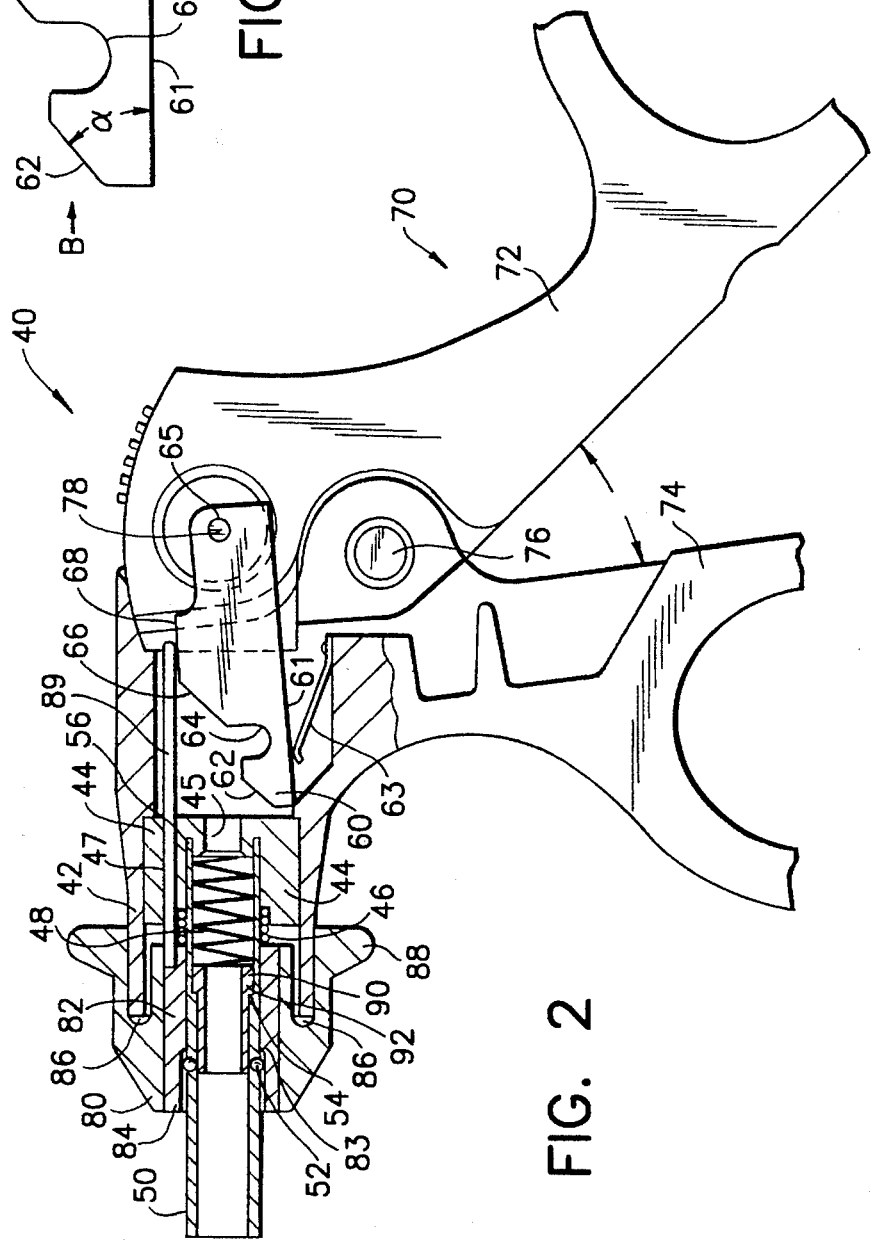
FIG. 2 is cross sectional view of a portion of the detachable proximal handle of the endoscopic instrument of FIG. 1.

Turning now to FIG. 2, the proximal handle 40 of endoscopic instrument 10 is shown uncoupled from the distal portion 20 of the endoscopic instrument. The handle 40 preferably includes a tube sleeve 50, a ball bearing lock 52 carried by the tube sleeve 50, a sleeve block 44 which carries the tube sleeve 50, a latch 60, a spring 63 for biasing the latch 60, an actuating means 70, a collar 80, an unlatching rod 89 coupled to the collar 80, a second spring 46 for biasing the collar 80 distally, a bushing 90, and a third spring 48 for biasing the bushing 90 distally. The actuating means 70 includes a fixed portion 74 and a lever portion 72 which is pivotally engaged to the fixed portion by a pivot pin 76. The lever portion 72 is hingedly coupled to the latch 60 at bore 65 about a pivot pin 78 in the lever portion 72 of the handle 40. The latch 60 is biased upwards by the spring 63.

As described in more detail below, the latch 60 is provided to engage and disengage (i.e., disengagably engage) the proximal end mating tip 27 of the push rod 28 (FIG. 1). Distal the latch 60, the sleeve block 44 is mounted in the mouth 42 of the handle 40 to carry the sleeve 50. The sleeve block 44 is provided with a central bore 45 coaxial with sleeve 50 for receiving the push rod 28 (FIG. 1) and a second bore 47 providing passage for the unlatching rod 89 which extends proximally from the collar 80. Distal of the sleeve block 44, the collar 80 engages the mouth 42 of the handle 40. The collar 80 is provided with an annular space 86 into which the mouth 42 extends. The collar 80 is provided with a central bore 82 having a stepped larger diameter portion 84 coaxial to the sleeve 50. As aforementioned, the collar 80 carries the unlatching rod 89, and is biased distally from the sleeve block 44 by a spring 46 which seats on the sleeve block 44. The collar 80 is therefore free to slide (from the position shown in FIG. 1) proximally over the sleeve 50 and the mouth 42 (and against spring 46) to move the unlatching rod 89 against the latch 60 as shown in FIG. 2 and described in more detail below. In order to facilitate manual sliding of the sliding collar 80, a flange 88 is provided on the collar 80. The flange extends radially outward from the collar 80 as shown in FIGS. 1 and 2.

Sleeve 50 of handle 40 is provided with a ball bearing lock 52 (described in detail below with reference to FIG. 5) which engages a groove 138 (described in detail below with reference to FIG. 4) in the proximal end 38 of tube 22 as shown in FIG. 1. As shown in FIG. 2, when the tube of the distal portion of the endoscopic instrument is not in place, an inner bushing 90 is biased by a spring 48 which causes the bushing 90 to engage ball bearing lock 52. In that position, the ball bearing lock 52 holds the collar 80 in the retracted position. In the retracted position, the latch 60 is pressed down against spring 63 by the action of unlatching rod 89. The sliding collar 80 must be retracted to the position shown in FIG. 2 before the proximal end mating tip 27 of push rod 28 (FIG. 1) can be released from latch 60. In this position, the larger diameter portion 84 of central bore 82 receives the balls from the ball bearing lock 52. When the tube 22 (FIG. 1) is withdrawn from sleeve 50, the bushing 90 extends distally under the bias of spring 48 and keeps the balls in the larger diameter portion 84. Movement of bushing 90 is limited by a shoulder 92 which engages a neck 54 of sleeve 50 described in more detail below with reference to FIG. 5. Shoulder 83 of collar 80 which is adjacent the larger diameter 84 of inner bore 82 keeps the collar 80 in the retracted position shown in FIG. 2 until a tube 22 is inserted in sleeve 50. As will be described in more detail below, insertion of a tube 22 into sleeve 50 moves the balls of ball bearing lock 52 away from the shoulder 83.

Figure 3A:
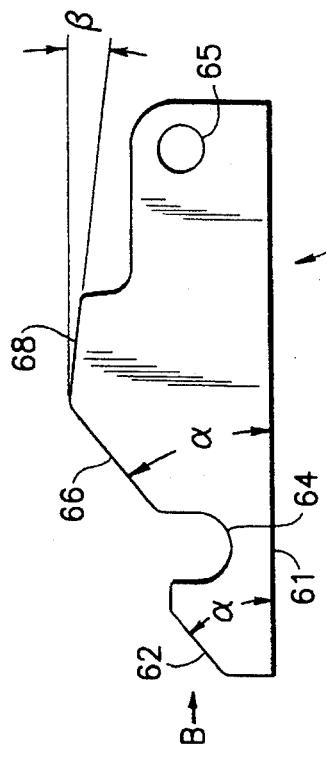
FIG. 3a is a side elevation view of one embodiment of push rod latch of the detachable proximal handle of FIG. 2.
Figure 3B:
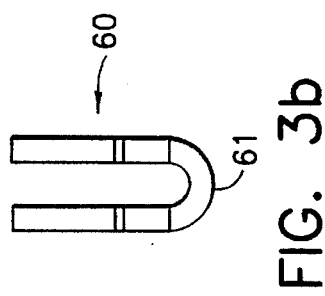

FIGS. 3a and 3b show details of the latch 60. In particular, with reference to FIGS. 1, 2, 3a and 3b, a preferred latch 60 is formed as a U-shaped hook having inclined edges 62, 66, 68, a pivot bore 65, and a hook recess or notch 64. As can be appreciated by comparing FIGS. 1 and 2 with the benefit of the details shown in FIGS. 3a and 3b, a bottom edge 61 of the latch 60 is biased by spring 63 which urges it upward. When urged upward, the latch 60 engages within its hook recess or notch 64 the proximal end mating tip 27 of the push rod 28. The inclined edge 66 which is preferably set at an angle α of approximately 40°, is engaged by the unlatching rod 89 when the sliding collar 80 is retracted as shown in FIG. 2. The rod 89 rides along the inclined edge 66, thereby forcing the latch 60 down against spring 63 as it pivots about pin 78 in bore 65. At the upper end of edge 66, another inclined edge 68 having an angle B of approximately 6° allows the rod 89 to move further inward without moving latch 60. Thus, in the retracted position, the sliding collar 80 in conjunction with its attached unlatching rod 89, causes the latch 60 to pivot down approximately 6°. It is noted that an additional inclined edge 62 having an angle α of approximately 40° is also provided for easy engagement of the proximal end mating tip 27 of push rod 28 as described in detail below.

Figure 4A:
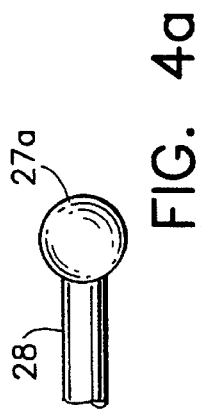
FIG. 4a is a perspective view of a ball tip on the proximal end of the push rod.
Figure 4B:
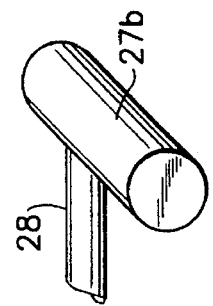
FIG. 4b is a perspective view of a T-bar tip on the proximal end of the push rod.
Figure 4:
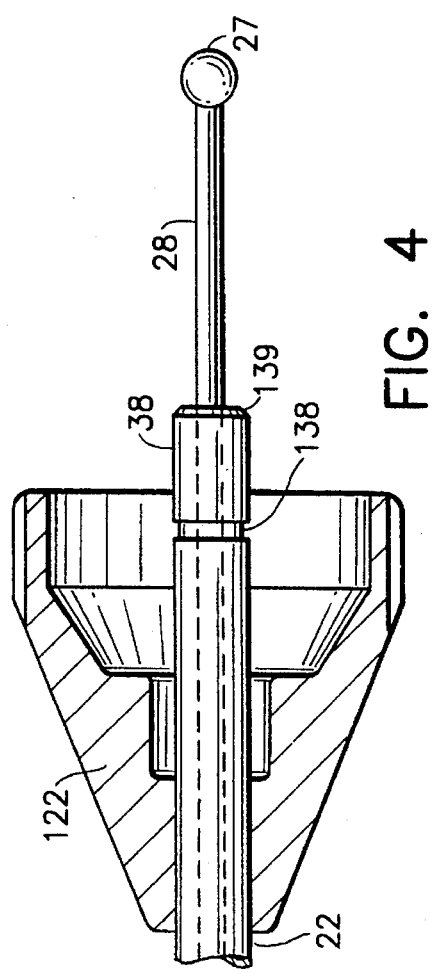
FIG. 4 is a side elevation view of the proximal portions of the tube and push rod of the detachable distal portion of the endoscopic instrument of FIG. 1.
Figure 5:
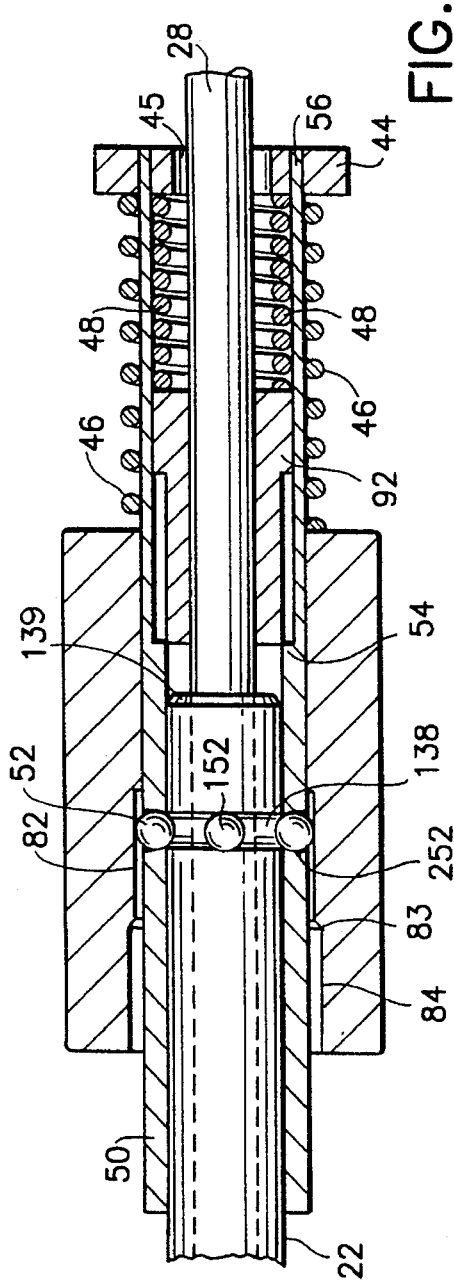
FIG. 5 is a cross sectional view of the ball lock and biased bushing of FIG. 2 with a tube inserted therein.

FIG. 4 shows details of the proximal end 38 of the tube 22 and the proximal end of the push rod 28. The tube 22 is provided with a ferrule 122 extending outwardly from the tube 22. The ferrule 122 is generally conical and, as shown in FIG. 1, is dimensioned to fit over the distal end of the sliding collar 80 and the sleeve 50 of the proximal handle 40 of the endoscopic instrument. The tube 22 is also provided with a radial circumferential groove 138 which is intended to engage the ball bearing lock 52 as seen in FIGS. 1 and 5. Proximal of the groove 138, the tube 22 is provided with a tapered edge 139 which engages bushing 90 as shown in FIGS. 1 and 5. The push rod 28 extends through the tube 22 and beyond the proximal end 38 of the tube 22 to a proximal end mating tip 27 which engages the latch 60 as described above. FIGS. 4a and 4b show two embodiments of the proximal end mating tip 27, one being spherical (27a) and the other being a T-bar (27b). The spherical ball tip 27a (FIG. 4a) is preferred since it allows for coupling in any rotational position and allows the ferrule 122 with attached tube 22 to be rotated with respect to the handle 40 in order to rotate the position of the end effector (FIG. 1). The T-bar tip 27b (FIG. 4b), on the other hand, does not allow rotation of the distal portion 20 of the endoscopic instrument relative to the handle portion 40.

FIG. 5 shows details of the ball bearing lock 52, the bushing 90, and the central bore 82 of the sliding collar 80. As seen in FIG. 5, sleeve 50 is provided with a plurality of tapered radial bores 252 which taper inward to receive a corresponding number of balls 152. The taper in bores 252 is designed to prevent balls 152 from passing completely through the bores 252, but to permit the balls to extend at least partially therethrough. The central bore 82 of the sliding collar 80 (FIGS. 1 and 2) holds the balls 152 in tapered radial bores 252, whereby the balls extend into the interior of sleeve 50 to engage the groove 138 in the proximal end of the tube 22. When the sliding collar 80 is retracted as shown in FIG. 2, the balls 152 are permitted access to the larger diameter portion 84 of the bore 82. When located in the larger diameter portion 84, the balls release the tube 22 by rolling over the inclined edge 140 of groove 138 as the tube 22 is withdrawn from sleeve 50. The bushing 90, biased by spring 48, follows the tube 22 as it is withdrawn from sleeve 50 and prevents the balls 152 from re-entering the interior of sleeve 50. Thus, once the sliding collar 80 is retracted and the tube 22 is removed from the sleeve 50, the balls 152, held in place by bushing 90 continue to occupy the larger diameter 84 of bore 82 and prevent the collar 80 from moving forward. As mentioned briefly above, sleeve 50 is provided with a larger diameter portion 56 at its proximal end within which the bushing 90 and the spring 48 are mounted. The bushing 90 has shoulder 92 which thus engages a neck 54 of the sleeve 50 so that the bushing 90 is limited in its movement to the positions shown in FIGS. 1 and 2. By properly choosing the strength of the spring 48, the bushing 90 can "auto-eject" the tube 22 and the push rod 28. For example, when collar 80 is pulled back to the retracted position as shown in FIG. 2, the latch 60 is uncoupled from the push rod tip 27 and the ball bearings 152 are given access to the larger diameter portion 84 of bore 82. At this point, there is nothing preventing the tube 22 and push rod 28 from being removed from the handle 40. If the spring 48 is sufficiently strong, the bushing 90 will be pushed forward and will push the tube 22 out of the sleeve 50. As the groove 138 on the tube 22 moves out of ball bearing lock 52, the balls 152 ride over the inclined edge 140 of the groove 138 and enter the larger diameter 84 portion of the bore 82. After the tube 22 and the push rod 28 have been ejected, the bushing 90 keeps the balls 152 in the larger diameter 84 section of the bore 82, thus holding the collar 80 in the retracted position.

Figure 6:
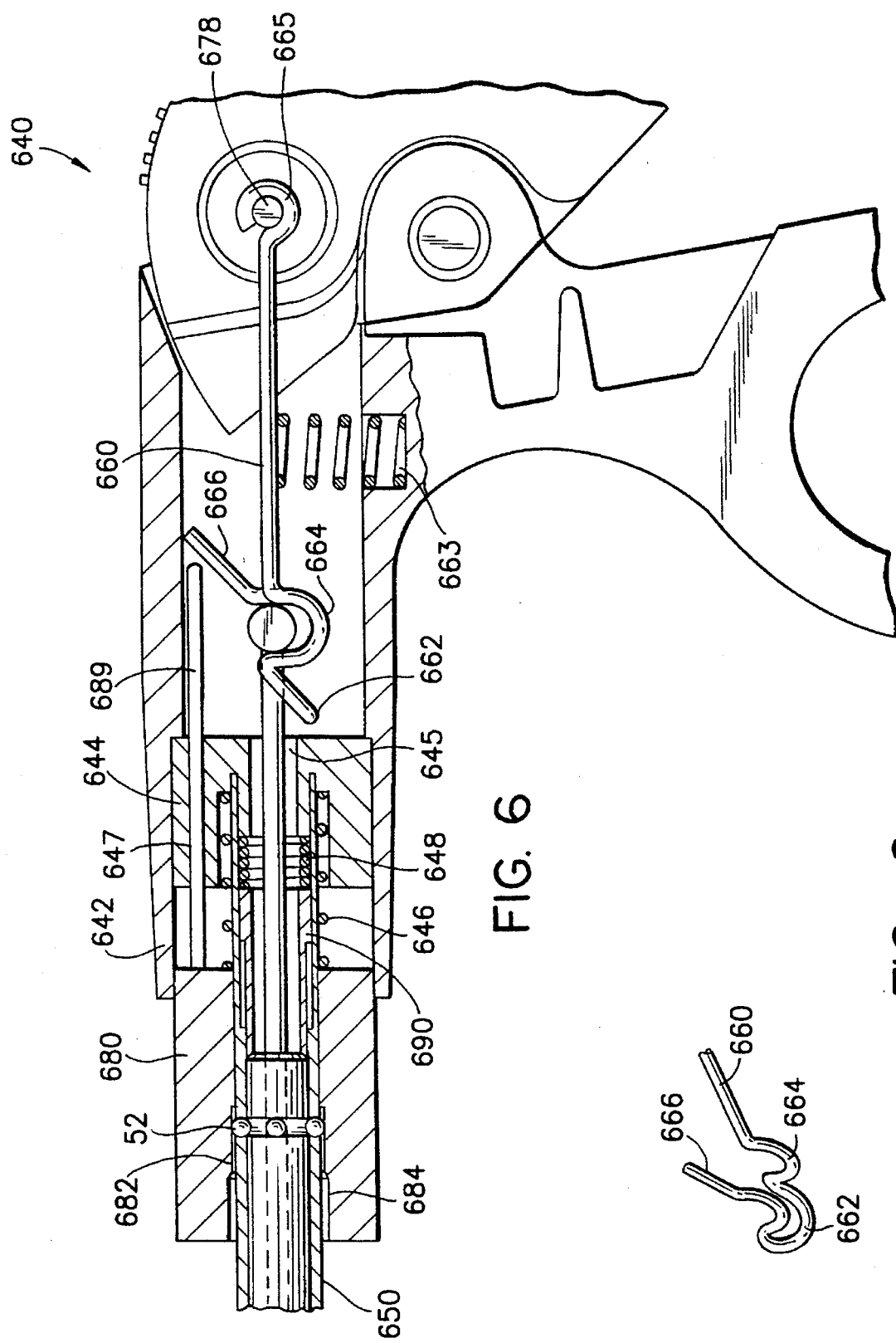
FIG. 6 is a view similar to FIG. 2 but of an alternate embodiment of the invention.
Figure 6A:
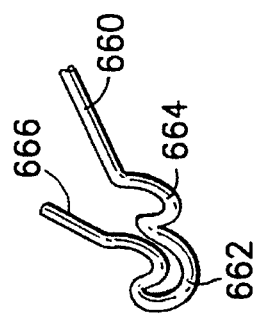
FIG. 6a is a perspective view of the latch of FIG. 6.

FIG. 6 shows an alternate embodiment of handle portion 640 which is in many respects similar to the handle embodiment 40 described above with reference to FIGS. 1–5. Here, however, the sliding collar 80 of the embodiment of FIGS. 1–5 is replaced by a smaller retractable collar 680 which slides into the mouth 642 of the handle 640. The retractable collar 680 is provided with an inner bore 682, a larger diameter portion 684, and an unlatching rod 689 which all function essentially the same way as the inner bore 82, the larger diameter portion 84, and the unlatching rod 89 of the embodiment of FIGS. 1–5. The sleeve block 644, the central bore 645, the second bore 647, the springs 646 and 648, the bushing 690, and the tube sleeve 650 also function in essentially the same way as the sleeve block 44, the central bore 45, the second bore 47, the springs 46 and 48, the bushing 90 and the tube sleeve 50 described above in the embodiment of FIG. 1–5. In the embodiment of FIG. 6, however, the latch 660 (also seen in FIG. 6a) is formed as a wire frame with a proximal eyelet 665, and a series of distal U-bends 664, 662 terminating in a free end 666. Eyelet 665 pivots on pin 678 in a manner similar to the latch described in the embodiment of FIGS. 1–5. U-bends 664 form a hook recess analogous to the recess 64 in latch 60 described above and U-bend 662 forms an inclined edge analogous to the inclined edge 62 of the latch 60 described above. The free end 666 of latch 660 is also inclined in an analogous manner to the inclined edge 66 of the latch 60 described above, and is engaged by the unlatching rod 689 when the retractable collar 680 is moved into the mouth 642. The latch 660 is biased upward by a spring 663 which is also analogous to spring 63 described above with reference to FIGS. 1 and 2.

Figures 6B, 6C:
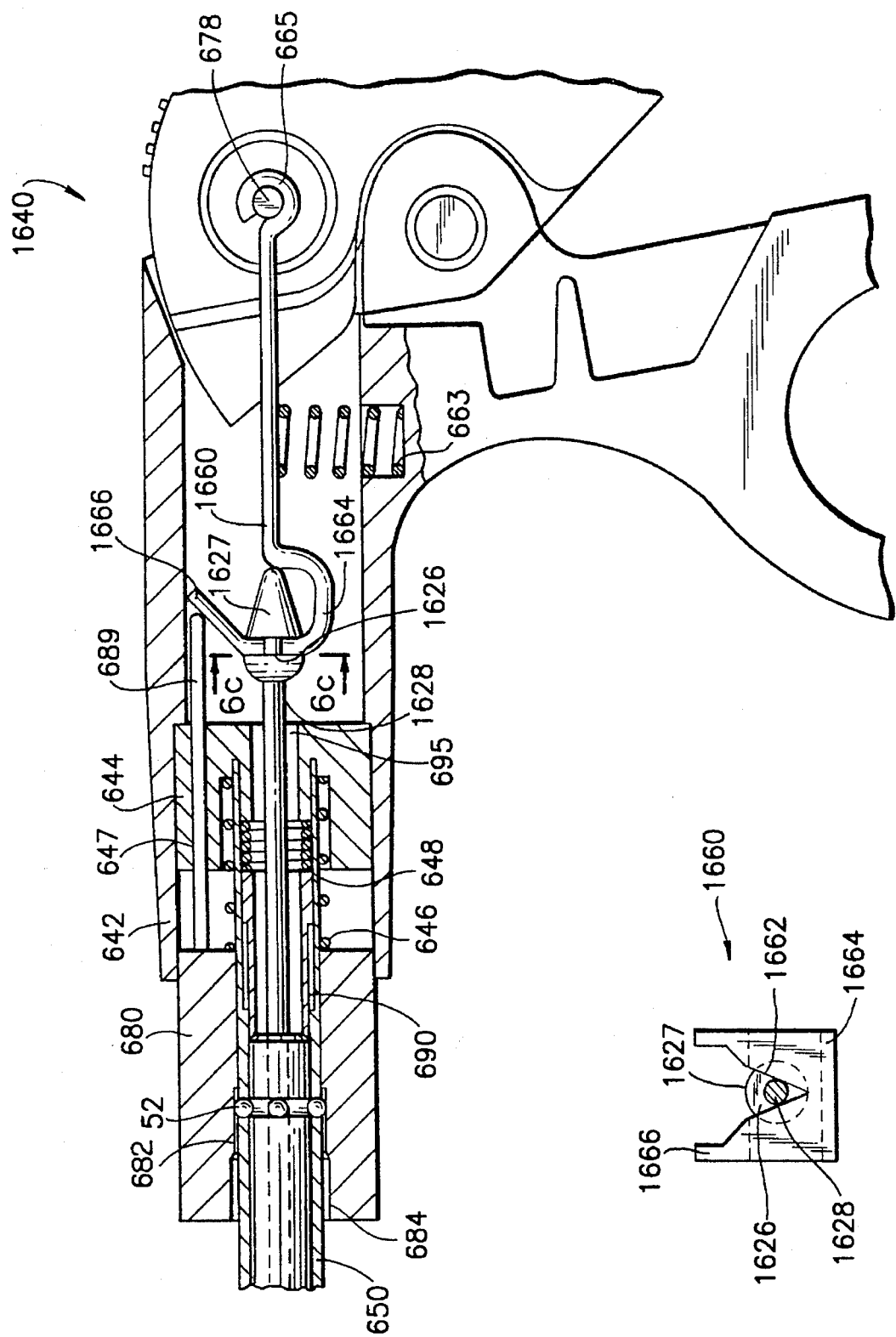
FIG. 6b is a view similar to FIG. 6 but of another embodiment of the invention utilizing a different push rod coupling means.
FIG. 6c is a cross sectional view along line 6—6 of FIG. 6b.

FIG. 6b shows an alternate embodiment of handle portion 1640 which is in many respects similar to the handle embodiment 640 described above with reference to FIG. 6. Here, however, while the latch 1660 (also seen in FIG. 6c) is formed in its distal part with a U-bend 1664 which forms a hook recess analogous to the recess 664 in latch 660 described above, a generally V-shaped notch 1662 forms an inclined edge somewhat analogous to the inclined edge 662 of the latch 660 described above. The free end 1666 of latch 1660 is also inclined in an analogous manner to the inclined edge 666 of the latch 660 described above, and is engaged by the unlatching rod 689 when the retractable collar 680 is moved into the mouth 642. The V-shaped notch 1662 is designed to engage a push rod tip 1627 at the proximal end of push rod 1628. In this embodiment, the push rod tip 1627 is formed as a generally conical member with a circumferential groove 1626. As will be appreciated, when the conical tip 1627 presses against the V-shaped notch 1662, the inclined edges of the V-shaped notch are engaged by the surface of the conical tip to push the latch 1660 down against spring 663 in a manner analagous to the latch 660 described above. As the conical tip 1627 moves farther into the handle portion 1640, its groove 1626 passes over the V-shaped notch and the latch 1660 is then biased upwards into the grove to assume the position shown in FIGS. 6b and 6c. Unlatching is accomplished in the same manner as with latch 660 described above.

Turning to FIG. 7, another embodiment of the invention is seen. In FIG. 7, the latch 660 and its parts are the same as in the embodiment of FIG. 6. On the other hand, the ball bearing lock and sliding collar of the embodiments described above with reference to FIGS. 1–6 are replaced by a blade lock 752 in the handle 740 of the instrument. FIGS. 7a and 7b show the details of the blade lock 752 which includes a tube sleeve 750, a sliding blade 754 having a flange 753, and springs 751 and 755. The tube sleeve 750 is provided for receiving the tube 22 as shown, and the sliding blade 754 is substantially perpendicular to and transects the sleeve 750. The sliding blade 754 is provided with a hole 756 large enough to accommodate the tube 22 of the distal portion of the endoscopic instrument when the hole 756 is aligned coaxially with the sleeve 750 and the flange 753 of the blade 754 is biased by the spring 751. The spring 751 effectively biases the blade 754 so that the center of the hole 756 in the blade is off the axis of sleeve 750, thereby causing a portion of the inside edge of the hole 756 to engage the tube 22. By aligning the positions of the blade 754 and the locking groove 138 in the tube 22, an edge of the hole 756 will engage the groove 138 as shown in FIGS. 7, 7a, and 7b. Pressing the flange 753 against the spring 751 moves the blade 754 so that the hole 756 is coaxial with the sleeve 750, thereby allowing the tube 22 to be removed from sleeve 750.

As shown in FIGS. 7, 7a, and 7b, the blade 754 is preferably provided with a second hole 758 which is engaged by a release button 757 which is biased by the spring 755. As shown, the second hole 758 is connected to hole 756, but as will be appreciated from the following description, this connection is not essential. The second hole 758 is provided with a broad shouldered opening 759, and the release button 757 is provided with a narrow diameter portion 767 and a wide diameter portion 777. The wide diameter portion 777 of the release button 757 is wider than the diameter of the second hole 758, but is narrower than the broad shouldered opening 759. Considering FIGS. 7a and 7b, it will be appreciated that when the flange 753 is pressed against the spring 751, blade 754 is moved so that the hole 756 is coaxial with the sleeve 750, and the broad shouldered portion 759 of the second hole 758 is brought into alignment with the wide diameter portion 777 of release button 757. In this position, the spring 755 which biases the release button 757 moves the wide diameter portion 777 of the button 757 into the broad shouldered opening 759 of the second hole 758, thereby holding the blade 754 in a position where hole 756 is aligned coaxially with the sleeve 750. It will also be appreciated that when the blade is held in this position, the release button 757 extends distally out from the blade lock 752. As shown in FIG. 7, the tube 22 is provided with a broad faced ferrule 722 which presses against the release button 757 when the tube 22 is inserted into the sleeve 750 of the blade lock 752. When the release button 757 is so pressed, the wide diameter portion 777 is moved against the spring 755 and releases the broad shouldered portion 759 so that the blade 754 is free to move up under the action of spring 751 acting on flange 753. When the blade 754 moves to this position, an edge of the hole 756 engages the groove 138 in tube 22 and the narrow diameter portion 767 of the release button engages the second hole 758 holding the release button 757 in the retracted position as shown in the Figures.

As mentioned above, the tube 22 and the push rod 28 must both be released from the handle 740 so that the distal portion of the endoscopic tool may be removed from the handle portion. In the embodiment of FIG. 7, a release switch 780 is provided for this purpose. The release switch 780 is coupled to the unlatching rod 789 which functions in the same manner as the unlatching rod 689 described above with reference to FIG. 6. When the switch 780 is pressed down and slid back, it simultaneously engages flange 753 of the blade 754 while causing the unlatching rod 789 to engage end 666 of latch 660 which causes the release of the push rod 28. Depending on the size of button 757 and strength of spring 755, the push rod 28 in the tube 22 with ferrule 722 may be auto-ejected from the handle 740.

The blade lock embodiment shown in FIG. 7 may also be provided with a ball 794 radially biased by spring 796 to engage one of a plurality of longitudinal grooves 792 on tube 22. In addition, ferrule 722 may be provided with a gripping surface 723 such that it may be easily gripped to rotate the tube 22. The biased ball 794 and longitudinal grooves 792 serve to limit the rotation of the tube 22 by providing "click-stops" as the tube is rotated by twisting the ferrule. It will be appreciated that this kind of arrangement can be applied to any of the handle embodiments shown so long as the engaging tip 27 of the push rod 28 is free to rotate within the latch 660.

Figure 8A:
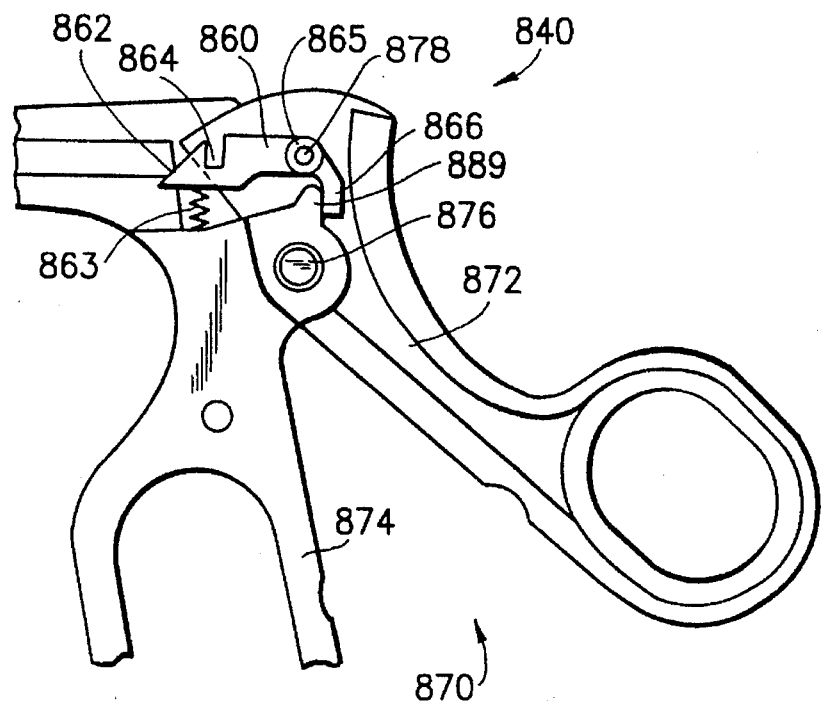
FIGS. 8a and 8b are schematic views similar to FIG. 6 but utilizing an alternative latching mechanism.
Figure 8B:
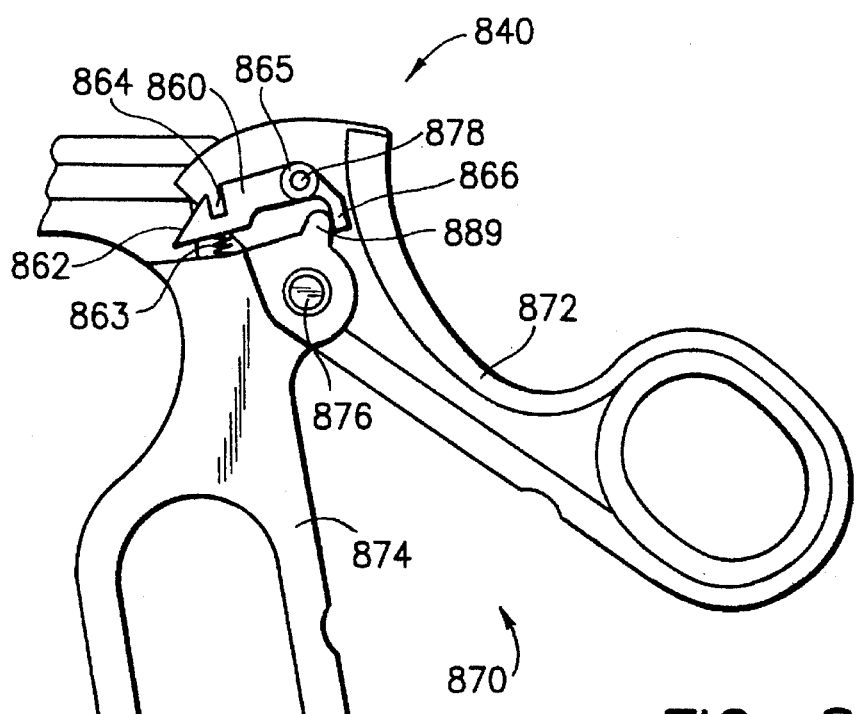

FIGS. 8a and 8b show another embodiment of a push rod coupling latch. Like the latches 60 and 660 described above, the latch 860 of FIGS. 8a and 8b is pivotally coupled to the lever portion 872 of the actuating means 870 in the handle 840 by a pivot pin 878. As with the other latches, latch 860 is biased upwards by spring 863 to engage the mating tip of a push rod not shown in FIGS. 8a and 8b. Unlike the other latches, however, latch 860 is provided with a proximal downward projection 866 on the opposite side of pivot pin 878 so that movement of this projection 866 causes the latch 860 to pivot about pin 878. The fixed portion 874 of the actuating means 870 is provided with an unlatching cam 889 extending substantially radially from the point 876 about which the lever portion 872 pivots with respect to the fixed portion 874. As can be seen by comparing FIGS. 8a and 8b, when the lever portion 872 is rotated away from the fixed portion 874 beyond a certain amount, the downward rear projection 866 of latch 860 is engaged by unlatching cam 889 which causes the latch 860 to pivot down against spring 863 to unlatch the mating tip of a push rod in a manner similar to the latches described above. It will be appreciated that in this embodiment of the latch, no unlatching rod is necessary. Moreover, as will be appreciated by those skilled in the art, once the tube lock is released, removal of the tube carrying the push rod will automatically release the push rod latch shown in FIGS. 8a and 8b.

Figure 9:
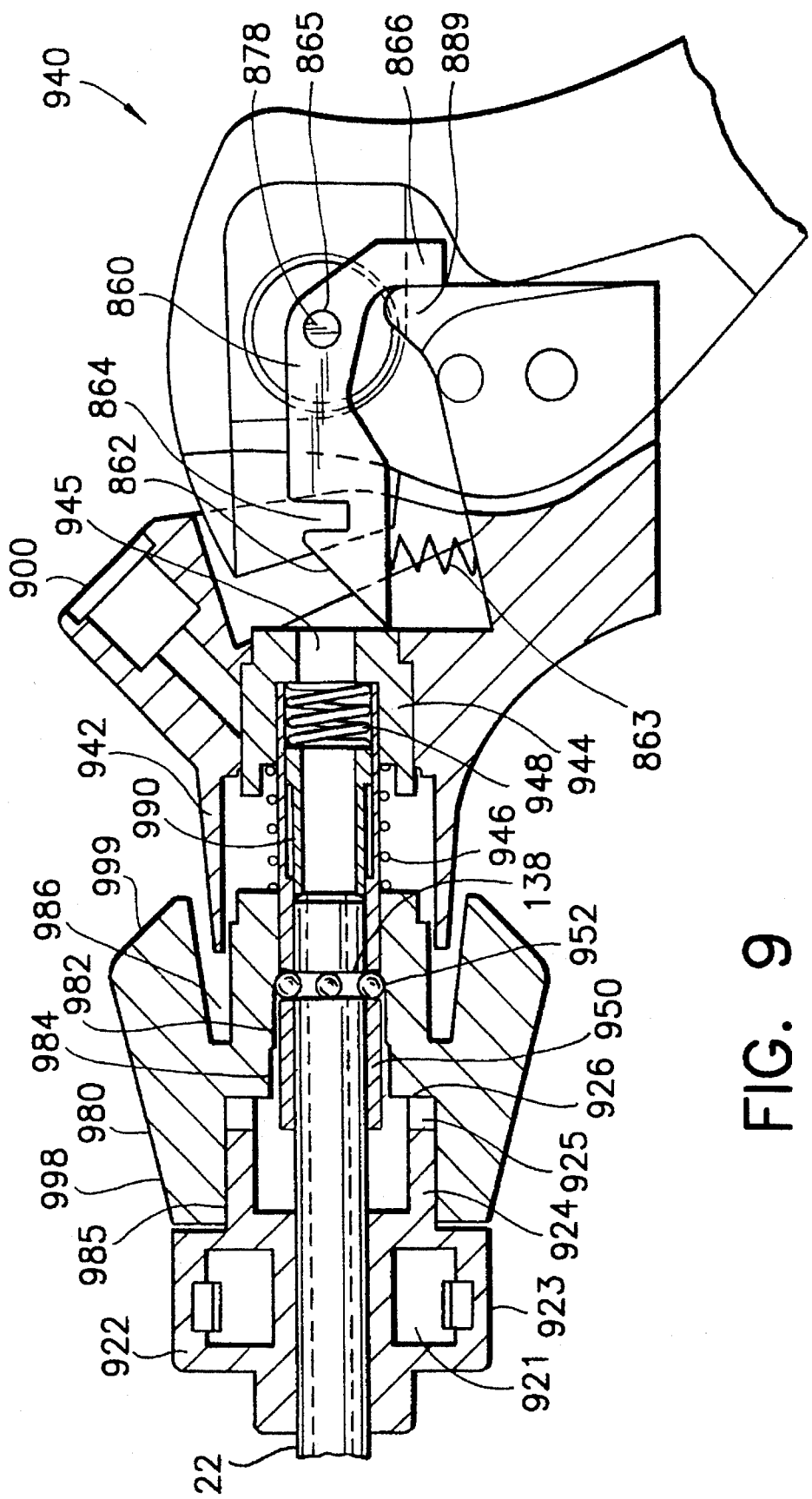
FIG. 9 is a view similar to FIG. 6 of a preferred embodiment of the invention utilizing the latching mechanism of FIGS. 8a and 8b, and a different

FIG. 9 shows a preferred embodiment of handle portion 940 incorporating the push rod latch 860 of the embodiment described above with reference to FIGS. 8a and 8b. The tube coupling arrangement of this embodiment is substantially similar to the tube coupling arrangements of FIGS. 1–6. In particular, the tube coupling arrangement of handle 940 preferably includes a tube sleeve 950, a ball bearing lock 952 carried by the tube sleeve 950, a sleeve block 944 which carries the tube sleeve 950, a collar 980, a first spring 946 for biasing the collar 980 distally, a bushing 990, and a second spring 948 for biasing the bushing 990 distally. The sleeve block 944 is mounted in the mouth 942 of the handle 940 to carry the sleeve 950 and is provided with a central bore 945 coaxial with sleeve 950 for receiving a push rod 28 (see FIG. 1). Distal of the sleeve block 944, the collar 980 is provided with an annular space 986 into which the mouth 942 of the handle can extend when the collar 980 is retracted as discussed below. The collar 980 is provided with a generally tapered cross section 998 which increases in diameter as it extends proximally to facilitate gripping of the collar in order to retract it, and a second proximal tapered surface 999 which decreases in diameter as it extends proximally and provides a knurled surface or the like to facilitate rotation as discussed below. In this embodiment, collar 980 is also free to rotate axially with respect to handle portion 940 as will be described in detail below. The collar 980 is also provided with a central bore 982 having a stepped larger diameter portion 984 coaxial to the sleeve 950 and a distal larger diameter portion 985 for receiving a portion of a tube ferrule 922 which is described in detail below. As aforementioned, the collar 980 is biased distally from the sleeve block 944 by a spring 946 which seats on the sleeve block 944. The collar 980 is therefore free to slide over the sleeve 950 (and against spring 946) from the position shown in FIG. 9 to a proximal position in order to release the ball bearings 952 in a manner substantially the same as described above with reference to collar 80 of FIG. 2. It will be appreciated that collar 980 is not provided with an unlatching rod since none is necessary with the latch embodiment 860 which is described in detail above with reference to FIGS. 8a and 8b.

As shown in FIG. 9, tube 22 is provided with a tube ferrule 922. The ferrule 922 has a large diameter portion 923 and a smaller diameter portion 924 which is provided with peripheral engaging teeth 925. If the distal portion of the endoscopic instrument is to be reused, the large diameter portion 923 is used to house a use counter 921 as described in parent application U.S. Ser. No. 07/998,951, so that the number of uses of the distal portion may be tracked. Such a use counter may alternatively be incorporated into collar 980 to track the number of uses of the handle portion 940. The smaller diameter portion 924 of the ferrule 922 is received by the distal large diameter opening 985 of the collar 980. The distal large diameter opening 985 of collar 980 is also provided with annular engaging teeth 926 which engage the peripheral teeth 925 of the ferrule 922. Since the collar 980 is free to rotate axially relative to handle portion 940 as mentioned above, it will be appreciated that through the engaging teeth 925, 926, the rotation of the collar 980 will cause a rotation of the ferrule 922. In turn, since the ferrule 922 is attached to the tube, rotation of the ferrule 922 causes the tube 22 to rotate and to effect rotation of the end effectors (not shown) coupled to the distal end of tube 22. Of course, in order to facilitate rotation, the push rod should be provided with a ball joint at its proximal end (as shown in FIG. 4) so that rotation of the tube is uncoupled from rotation of the handles.

The handle portion 940 of the embodiment FIG. 9, is also preferably provided with a electrical coupling 900 for applying a cauterizing current to the end effectors (not shown). In this embodiment, the sleeve block 944, the sleeve 950 and the tube 22 are all made of conductive material. An electrical source (not shown) connected to electrical connection 900 will therefore couple electrically with the end effectors via tube 22, sleeve block 944, and sleeve 950.

There have been described and illustrated herein several embodiments of an endoscopic instrument with a separable proximal handle and distal portions. While particular embodiments of the invention have been described, it is not intended that the invention be limited thereto, as it is intended that the invention be as broad in scope as the art will allow and that the specification be read likewise. Thus, while particular latches have been disclosed, it will be appreciated that other latch configurations could be utilized. Also, while a ball lock and blade lock for the tube have been shown, it will be recognized that other types of tube locks could be used with similar results obtained. It will also be recognized that the embodiments of tube locks are not dependent on the particular embodiments of latches, and any of the latches disclosed may be used with any of the tube locks disclosed. Moreover, while particular configurations have been disclosed in reference to the push rod mating tip, it will be appreciated that other configurations could be used as well. Further, it will be appreciated that while it is intended that the distal portion of the endoscopic instrument will be used several times and then discarded, while the proximal handle portion will be used many times before it is discarded, the invention is not limited to distal portions or handle portions which will be reused. Thus, it is certainly possible that either the distal portion or the handle portion will have a single use. It will therefore be appreciated by those skilled in the art that yet other modifications could be made to the provided invention without deviating from its spirit and scope as so claimed.

We claim:

1. An endoscopic instrument, comprising:
   a) a distal portion; and
   b) a proximal handle portion, wherein,
      said distal portion includes
         a hollow tube having a proximal and a distal end, said proximal end of said tube provided with tube coupling means for coupling said hollow tube to said handle portion,
         a rod extending at least partially through said hollow tube and having a proximal and a distal end, said proximal end of said rod provided with rod coupling means for coupling said rod to said handle portion,
         an end effector coupled to said distal end of said tube and said distal end of said rod, and
      wherein said handle portion includes,
         a handle body, said handle body provided with handle coupling means for connecting with said tube coupling means to thereby couple said hollow tube to said handle body, said handle coupling means comprising a sleeve with a biased locking member and said tube coupling means connecting to said handle coupling means by inserting said tube into said sleeve until said biased locking member engages said tube coupling means;
         actuating means for imparting reciprocal motion to said rod relative to said tube, said actuating means provided with actuator coupling means for connecting with said rod coupling means to thereby couple said rod to said actuating means.

2. An endoscopic instrument according to claim 1, wherein:
   said tube coupling means comprises a circumferential groove on said tube.

3. An endoscopic instrument according to claim 2, wherein:
   said biased locking member comprises a ball lock, and said tube coupling means connects to said handle coupling means by inserting said tube into said sleeve until said ball lock engages said groove.

4. An endoscopic instrument according to claim 3, wherein:
   said sleeve includes a plurality of radial tapered bores and said ball lock comprises a plurality of ball bearings seated in said bores.

5. An endoscopic instrument according to claim 4, wherein:
   said sleeve is provided with a collar surrounding said ball bearings, wherein said collar holds said ball bearings in said tapered bores.

6. An endoscopic instrument according to claim 5, wherein:
   said collar is provided with a first surface portion having a proximally rising inclined surface.

7. An endoscopic instrument according to claim 6, wherein:
   said collar is provided with a second surface portion proximal of said first surface portion, said second surface portion having a proximally falling inclined surface.

8. An endoscopic instrument according to claim 5, wherein:
   said tube is provided with a proximal ferrule means for engaging said collar.

9. An endoscopic instrument according to claim 8, wherein:
   said collar is provided with first engagement means for engaging said ferrule means when said collar is in a first position, and said ferrule means is provided with second engagement means for engaging said collar.

10. An endoscopic instrument according to claim 9, wherein:
    said collar is rotatable around said sleeve,
    said tube is rotatable within said sleeve, and
    said ferrule means is rotationally fixed relative to said tube, wherein rotation of said collar in said first position results in rotation of said tube.

11. An endoscopic instrument according to claim 5, wherein:
    said collar is provided with a stepped internal throughbore and is slidable relative to said sleeve such that sliding said collar from a locking position to a releasing position allows said ball bearings to partially exit said tapered bores.

12. An endoscopic instrument according to claim 11, wherein:
    said collar is biased to said locking position.

13. An endoscopic instrument according to claim 12, wherein:
    said sleeve is provided with a sliding internal bushing slidable from an extended position to a retracted position and biased to said extended position, wherein said bushing engages said ball bearings and presses said ball bearings partially out of said tapered bores.

14. An endoscopic instrument according to claim 13, wherein:
    said bushing is moved from said extended position to said retracted position by said tube when said tube is inserted into said sleeve.

15. An endoscopic instrument according to claim 2, wherein:
    said handle coupling means comprises said sliding blade and a sleeve having a longitudinal throughbore for receiving said tube and a diametrical throughbore for receiving a sliding blade, and
    said sliding blade has a hole large enough to receive said tube and said sliding blade is slidable through said diametrical throughbore from a releasing position wherein said tube is slidable through said sleeve to a locking position wherein said blade engages said groove.

16. An endoscopic instrument according to claim 15, wherein:
    said sliding blade is biased to said locking position.

17. An endoscopic instrument according to claim 16, wherein:
    said handle coupling means includes a biased pin having a large diameter portion and a small diameter portion,
    said sliding blade is provided with a biased pin receiving means for receiving said biased pin,
    said biased pin is movable from a first position wherein said large diameter portion engages said receiving means in said sliding blade when said blade is in said releasing position to a second position wherein said small diameter portion engages said receiving means in said sliding blade when said blade is in said locking position, said biased pin being biased to said first position, and said tube being provided with pin engagement means for moving said biased pin from said first position to said second position when said tube is slid through said sleeve to said locking position.

18. An endoscopic instrument according to claim 1, wherein:

said actuator coupling means comprises a latch means for locking and releasing said rod coupling means, said latch means being movable from a locking position to a releasing position.

19. An endoscopic instrument according to claim 18, wherein:

said actuator coupling means includes cam means for moving said latch means from said locking position to said releasing position.

20. An endoscopic instrument according to claim 19, wherein:

said latch means includes cam engaging means for engaging said cam means.

21. An endoscopic instrument according to claim 20, wherein:

said actuating means includes a first actuator member pivotally coupled to a second actuator member, said latch means is pivotally coupled to said first actuator member, and said cam means is provided on said second actuator member.

22. An endoscopic instrument according to claim 18, wherein:

said rod coupling means comprises a ball shaped tip on said proximal end of said rod.

23. An endoscopic instrument according to claim 18, wherein:

said rod coupling means comprises a projection perpendicular to said rod at said proximal end of said rod.

24. An endoscopic instrument according to claim 18, wherein:

said rod coupling means comprises a cone shaped tip on said proximal end of said rod.

25. An endoscopic instrument according to claim 24, wherein:

said cone shaped tip is provided with a circumferential groove.

26. An endoscopic instrument according to claim 18, wherein:

said latch means is biased to said locking position.

27. An endoscopic instrument according to claim 26, wherein:

said latch means is provided with a first edge and an unlocking member, said first edge being engagable by said unlocking member to move said latch to said releasing position.

28. An endoscopic instrument according to claim 27, wherein:

the unlocking member is connected to said handle coupling means.

29. An endoscopic instrument according to claim 27, wherein:

the unlocking member is a projection on said handle portion and engages said first edge when said actuating means is moved to an unlocking position.

30. An endoscopic instrument according to claim 18, wherein:

said latch means pivotally engages said actuating means.

31. An endoscopic instrument according to claim 18, wherein:

said latch means comprises a U-shaped member with a receiving notch, wherein said rod fits within said U-shaped member and said rod coupling means engages said receiving notch.

32. A handle for use with an endoscopic instrument having a tube, a push rod, a distal end effector, and means for coupling the tube and push rod to said handle, said handle comprising:

a) a handle body;

b) actuating means coupled to said handle body for imparting reciprocal motion to the push rod relative to the tube;

c) handle coupling means for releasably coupling the tube to said handle body;

d) actuator coupling means for releasably coupling the push rod to said actuating means; and e) biasing means coupled to said handle coupling means for biasing said handle coupling means into engagement with the tube when the tube is inserted into said handle.

33. A handle according to claim 32, wherein:

said handle coupling means includes a sleeve with a radially movable member, the tube being receivable by said sleeve and engaged by said radially movable member.

34. A handle according to claim 33, wherein:

said radially movable member comprises a ball bearing, and said sleeve includes a radial tapered bore receiving said ball bearing.

35. A handle according to claim 34, wherein:

said sleeve is provided with a collar, said collar having a stepped internal throughbore and being slidable from a locking position wherein said ball bearing is held in said tapered bore to a releasing position allowing said ball bearing to partially exit said tapered bore.

36. A handle according to claim 35, wherein:

said collar is biased to said locking position, and said sleeve is provided with an internal bushing slidable from an extended position to a retracted position and biased to said extended position wherein said bushing engages said ball bearing to move said ball bearing partially out of said tapered bore.

37. A handle according to claim 33, wherein:

said radially movable member comprises a blade, and said sleeve includes a diametrical slot receiving said blade.

38. A handle according to claim 37, wherein:

said blade is movable from a locking position to a releasing position and biased to said locking position.

39. A handle according to claim 38, wherein:

said handle coupling means includes a biased pin having a large diameter portion and a small diameter portion, said blade is provided with a biased pin receiving means for receiving said biased pin, said biased pin is movable from a first position wherein said large diameter portion engages said receiving means in said blade when said blade is in said releasing position to a second position wherein said small diameter portion engages said receiving means in said blade when said blade is in said locking position, said biased pin being biased to said first position, the tube being provided with pin engagement means for moving said biased pin from said first position to said second position when said tube is received by said sleeve.

40. A handle for use with an endoscopic instrument having a tube, a push rod, a distal end effector, and means for coupling the tube and push rod to said handle, said handle comprising:

a) a handle body;

b) actuating means coupled to said handle body for imparting reciprocal motion to the push rod relative to the tube;

c) handle coupling means for releasably coupling the tube to said handle body;

d) actuator coupling means for releasably coupling the push rod to said actuating means; and e) biasing means coupled to one of said handle coupling means and actuator coupling means for biasing one of said handle coupling means and said actuator coupling means into engagement with a respective one of the tube and the push rod when the tube and push rod are inserted into said handle, wherein said actuator coupling means comprises a latch which pivotally engages said actuating means and which moves from a locking position to a releasing position.

41. A handle according to claim 40, wherein:
said latch is biased to said locking position.

42. A handle according to claim 41, wherein:
said latch is provided with a first edge and an unlocking member, said first edge being engagable by said unlocking member to move said latch to said releasing position.

43. A handle according to claim 42, wherein:
said unlocking member is connected to said handle coupling means.

44. A handle according to claim 40, wherein:
said latch comprises a U-shaped member with a receiving notch.

45. A handle according to claim 40, wherein:
said actuating means includes cam means for moving said latch from said locking position to said releasing position.

46. A handle according to claim 45, wherein:
said latch includes cam engaging means for engaging said cam means.

47. A handle according to claim 46, wherein:
said actuating means includes a first actuator member pivotally coupled to a second actuator member, said latch is pivotally coupled to said first actuator member, and said cam means is provided on said second actuator member.

48. An endoscopic instrument connectable to a handle having actuating means, said endoscopic instrument comprising:

a) a hollow tube having a proximal and a distal end, said proximal end of said tube provided with tube coupling means for removably coupling said hollow tube to the handle;

b) a rod extending at least partially through said hollow tube and having a proximal and a distal end, said proximal end of said rod provided with rod coupling means for removably coupling said rod to the actuating means of the handle; and c) an end effector coupled to said distal end of said tube and said distal end of said rod, wherein said rod coupling means has a tapered tip on said proximal end of said rod so that said endoscopic instrument is quickly connectable to the handle by inserting said rod and tube into a sleeve on the handle until said tapered tip engages and couples with the actuating means of the handle.

49. An endoscopic instrument according to claim 48, wherein:
said tube coupling means comprises a circumferential groove on said tube.

50. An endoscopic instrument according to claim 48, wherein:
said rod coupling means comprises a ball shaped tip on said proximal end of said rod.

51. An endoscopic instrument according to claim 48, wherein:
said rod coupling means comprises a projection perpendicular to said rod at said proximal end of said rod.

52. An endoscopic instrument according to claim 48, wherein:
said rod coupling means comprises a cone shaped tip on said proximal end of said rod.

53. An endoscopic instrument according to claim 52, wherein:
said cone shaped tip is provided with a circumferential groove.

* * * * *